(12) United States Patent
Li et al.

(10) Patent No.: US 7,910,750 B2
(45) Date of Patent: Mar. 22, 2011

(54) ARTEMISININ (QINGHAOSU) DERIVATIVES, THEIR PREPARATION METHODS AND THEIR USE, AND PHARMACEUTICAL COMPOSITIONS CONTAINING THE SAME

(75) Inventors: Ying Li, Shanghai (CN); Jianping Zuo, Shanghai (CN); Zhongshun Yang, Shanghai (CN); Wenliang Zhou, Shanghai (CN); Yi Sui, Shanghai (CN); Junxia Wang, Shanghai (CN); Yu Zhang, Shanghai (CN); Yu Zhou, Shanghai (CN); Jinming Wu, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 291 days.

(21) Appl. No.: 11/883,652

(22) PCT Filed: Jan. 27, 2006

(86) PCT No.: PCT/CN2006/000182
§ 371 (c)(1),
(2), (4) Date: Sep. 17, 2007

(87) PCT Pub. No.: WO2006/081771
PCT Pub. Date: Aug. 10, 2006

(65) Prior Publication Data
US 2008/0139642 A1 Jun. 12, 2008

(30) Foreign Application Priority Data
Feb. 4, 2005 (CN) .......................... 2005 1 0023824

(51) Int. Cl.
C07D 323/04 (2006.01)
A61K 31/357 (2006.01)
(52) U.S. Cl. ...................................... 549/348; 514/450
(58) Field of Classification Search .................. 549/348; 514/450
See application file for complete search history.

(56) References Cited

U.S. PATENT DOCUMENTS

| 4,791,135 | A | 12/1988 | Lin et al. |
| 6,214,864 | B1 * | 4/2001 | Jain et al. ...................... 514/450 |
| 6,307,068 | B1 | 10/2001 | Li et al. |
| 2002/0187937 | A1 * | 12/2002 | Kawamura et al. .............. 514/12 |

FOREIGN PATENT DOCUMENTS

| CN | 1087638 | | 6/1994 |
| CN | 1122806 | | 5/1996 |
| CN | 1231288 | | 10/1999 |
| CN | 1239097 | | 12/1999 |
| CN | ZL 94113982.4 | | 2/2000 |
| CN | 1390840 | | 1/2003 |
| CN | 1390840 | A * | 1/2003 |
| CN | ZL 01113407.0 | | 9/2005 |

OTHER PUBLICATIONS

Yang et. al. Journal of Medicinal Chemistry 2005, 48, 4608-4617.*
O'Neill et. al. "Synthesis, Antimalarial Activity, Biomimetic Iron(II) Chemistry, and in Vivo Metabolism of Novel, Potent C-10-Phenoxy Derivatives of Dihydroartemisinin" Journal of Medicinal Chemistry 2001, 44, 58-68.*
International Search Report for PCT/CN2006/000180, mailed May 18, 2006.
Yang et al., "Synthesis and Immunosuppressive Activity of New Artemisinin Derivatives. 1.[12($\beta$ or $\alpha$)-Dihydroartemisininoxy]phen(ox)yl Aliphatic Acids and Esters," Journ. Of Med. Chem., 48(14): 4608-4617, (2005). (Abstract).
Cheng et al., "Molecular Docking and 3-D-QSAR Studies on the Possible Antimalarial Mechanism of Artemisinin Analogues," Bioorg. Med. Chem., 10(9): 2883-91 (2002). (Abstract).
Cheng et al., "Molecular Docking and 3-D-QSAR Studies on the Possible Antimalarial Mechanism of Artemisinin Analogues", Bioorganic & Medicinal Chemistry 10 (2002) 2883-2891, Dec. 17, 2001, 9 pages.

* cited by examiner

Primary Examiner — Rita J Desai
Assistant Examiner — David K O'Dell
(74) Attorney, Agent, or Firm — McKenna Long & Aldridge LLP

(57) ABSTRACT

The invention provides a type of artemisinin derivatives having following structure I, its preparation method and use, as well as a pharmaceutical composition containing such artemisinin derivatives and its use. The arteminsinin derivatives of the present invention and their pharmaceutical composition containing the artemisinin derivatives. have immunosuppressive activities and can be used more safely. The composition which comprises the artemisinin derivatives can be formulated into long-term dosage forms such as tablet, pellet and the like, and have wider productive and use value.

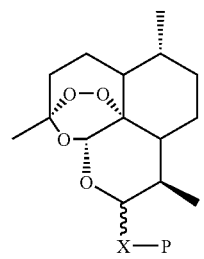

I

6 Claims, 4 Drawing Sheets

ARTEMISININ (QINGHAOSU) DERIVATIVES, THEIR PREPARATION METHODS AND THEIR USE, AND PHARMACEUTICAL COMPOSITIONS CONTAINING THE SAME

TECHNICAL FIELD

The present invention relates to the pharmaceutical chemistry field, particularly, to new terpene artemisinin derivatives, their preparation method and their use, and their pharmaceutical compositions containing the artemisinin derivatives.

BACKGROUND ART

Artemisinin, an effective component of the traditional Chinese drug Qinghao (*Artemisia annua* L.), is a peculiar sesquiterpenoid lactone having a peroxy group. The chemical structures of artemisinin and its derivative artesunate are:

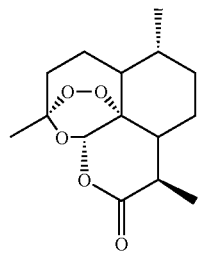 and 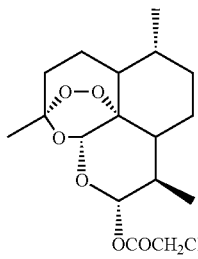 OCOCH₂CH₂COOH, respectively. Artemisinin not only has excellent antimalarial effect, but also is effective to other parasites (e.g. *Schistosoma japonicum* etc). Moreover it has been found to be immunosuppressive, and was once used in a clinical trial of lupus erythematosus with promising results. With the extension of related research works, it has been found that artesunate, a derivative of artemisinin, has a stronger immunosuppressive activity than artemisinin. It may achieve better therapeutic effects in the treatment of lupus erythematosus and some skin diseases. Although immunosuppressive effect of artesunate is stronger than that of artemisinin, the patients had to take it by intravenous injection in a long term of medication, so it is not convenient in administration. Cyclosporin A, a commonly used immunosuppressant, is expensive and deleterious to kidney and liver, so that some patients can not persist in the medication. Thus, the present inventor carries out a study for finding more effective and safer immunosuppressants.

DISCLOSURE OF THE INVENTION

One object of the invention is to provide a type of more effective and safer artemisinin derivatives having immunosuppressive activity.

Another object of the invention is to provide a preparation method of the above artemisinin derivatives.

Still another object of the invention is to provide a pharmaceutical composition containing the above artemisinin derivatives.

Still another object of the invention is to provide dosage forms of the above pharmaceutical composition containing the artemisinin derivatives of the present invention.

Still another object of the invention is to provide the medical use of the above artemisinin derivatives.

Still another object of the invention is to provide the medical use of the above pharmaceutical composition containing the artemisinin derivatives of the present invention.

According to an aspect of the invention, the present invention provides a type of artemisinin derivatives having the following structure I,

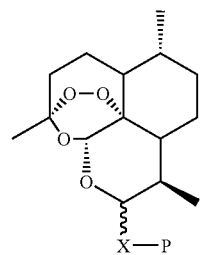

wherein,

X is O, O(CH₂)ₙ or OCHR₁, wherein the said R₁ is C₁-C₄ alkyl, CN, COOH, COOMe or COOEt, n is an integer of 1 to 4;

P is Ar—Y—Z or Ar—Z, wherein, Ar is a phenyl group or a naphthyl group, Y is O(CH₂)ₙ, OCHMe, C₁-C₄ alkyl, wherein n is an integer of 1 to 4, Z is H, halogen, OR', COOR' or CONHCH₂COOR', wherein R' is H, C₁-C₄ alkyl, o-methoxy phenyl or C₁-C₄ alkylamine group.

Specifically, for the artemisinin derivatives of the present invention,

X is O or OCH₂;

P is Ar—Y—Z, wherein, the said Ar is phenyl,

Y is O(CH₂)ₙ, OCHMe, C₁-C₄ hydrocarbyl, wherein n is 1 or 2,

Z is COOR', wherein, the said R' is H, Me, Et or o-methoxy phenyl.

Preferably, the artemisinin derivatives according to the present invention may be methyl 4-(12β-artemisininoxy)phenyl acetate; 4-(12β-artemisininoxy)phenyl acetic acid; ethyl 4-(12β-artemisininoxy)-phenoxy acetate; 3-(12β-artemisininoxy)phenoxy succinic acid; ethyl-[4-(12β-artemisininoxy) benzoyl] aminoacetate; methyl 2-[4-(12β-artemisininoxy) phenyl] propionate; o-methoxy-phenyl 2-[4-(12β-artemisininoxy)phenyl] propionate; ethyl 2-[4-(12β-artemisininoxy)phenoxy] propionate; 2-[4-(12β-artemisininoxy)phenoxy] propanoic acid; o-methoxy-phenyl 2-[4-(12β-artemisininoxy)phenoxy] propionate; o-methoxy-phenyl 2-[3-(12β-artemisininoxy)phenoxy] propionate, and 2-[4-(12β-artemisininoxy)phenyl] propanoic acid.

According to an aspect of the present invention, the present invention further provides a preparation method of the above artemisinin derivatives, which includes the following steps:

1) The dihydroartemisinin having the structure II or the acetyl dihydroartemisinin having the structure III is used as raw material, which react with phenol or alcohol containing carboxylic ester under an acidic catalysis condition, to obtain corresponding dihydroartemisinin ether products,

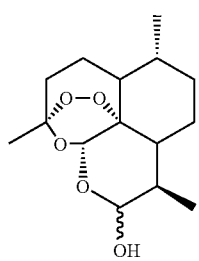

2) Then the dihydroartemisinin ether products are hydrolyzed to obtain intermediate products in a free acid form;

3) The intermediate products of free acid form of step 2) are further processed as final products, or, the method includes the following steps:

1) The dihydroartemisinin having the structure II or the acetyl dihydroartemisinin having the structure III is reacted with dihydric phenol under an acidic catalysis condition to obtain the compounds having the structure IV:

2) Then the above compounds having the structure IV are further modified to produce the final products.

The detailed preparation method can refer to the contents of the Chinese patents ZL 94113982.4, ZL 01113407.0 and patent application No. CN 99807416 of the same inventor.

The present invention further provides a pharmaceutical composition containing the above artemisinin derivatives, which comprises the compound of formula I or its pharmaceutically acceptable salts in a safe and effective dose range and the pharmaceutically acceptable carrier. Preferably, the said pharmaceutical composition comprises 1-85 weight percent of the artemisinin derivatives according to claim 1 or pharmaceutically acceptable salt thereof, 15-99 weight percent of excipient, 0-60 weight percent of other conventional auxiliary materials.

The "safe and effective dose" means: the amount of the compound is sufficient to evidently improve the patients condition and does not cause a serious side effect. The safe and effective dose of the compound may be determined according to the specific conditions, such as the age and weight of the subject, the adaptive diseases, the route of administration, the course of treatment and any related therapy, etc. Generally, an adult is administered by 0.1 mg/day to 500 mg/day in a single dose or multiple doses. The dosage should be reduced accordingly for children.

"Pharmaceutically acceptable carrier" refers to one or more compatible solid or liquid fillers or excipients, which are suitable for human body and must have sufficient high purity and low toxicity. "Compatible" herein means that each component of the composition can be blended with the compounds of the invention and with each other without obviously reducing the pharmacodynamic activity of the compound. The examples of pharmaceutically acceptable carrier partly includes sugars (e.g. glucose, sucrose, lactose, etc.), starch (e.g. maize starch, potato starch, etc.), cellulose and its derivatives (e.g. sodium carboxymethy cellulose, sodium ethyl cellulose, cellulose acetate, microcrystalline cellulose, etc.), acrylic acid resin, sodium polyacrylate, polyvidone, polyethylene glycol, polyoxyethylene monostearate, gelatin, silica gel, talc powder, stearic acid, magnesium stearate, calcium sulfate, vegetable oil (e.g. soybean oil, sesame oil, peanut oil, olive oil, etc). It also may be emulsifier (e.g. Tween®), moistening agent (e.g. sodium dodecyl sulphate), plasticizer (e.g. dibutyl sebacate), coloring agent, flavoring agent, stabilizer, preservative, nonpyrogenic water and the like. The selection of carrier for the compound of the present invention depends on the administration mode of the compound. Moreover, the persons skilled in the art can select the carrier suitable for a specific administration mode according to the prior art.

The present invention also provides dosage forms of the above pharmaceutical composition. The dosage form may be oral, parenteral, pernasal, lingual, ophthalmically, respiratory tract or rectal dosage form. Preferably, the dosage form is enteric coated pill, sublingual tablet, patch, suppository, cream, ointment or gels for skin use.

The present invention further provides the use of above artemisinin derivatives in preparing the drugs for treating or preventing diseases of immune system, and the use for treating or preventing diseases of immune system.

The present invention provides the use of the pharmaceutical composition containing the above artemisinin derivatives in preparing the drugs for treating or preventing diseases of immune system, and the use for treating or preventing diseases of immune system.

The artemisinin derivatives of present invention have effective immunosuppressive activities and can be used more safely. The compound containing the artemisinin derivatives can be manufactured into the dosage forms convenient for long term usage, such as tablets, pills and the like, and has more extensive production and use value.

EMBODIMENTS OF THE INVENTION

Figure 1:
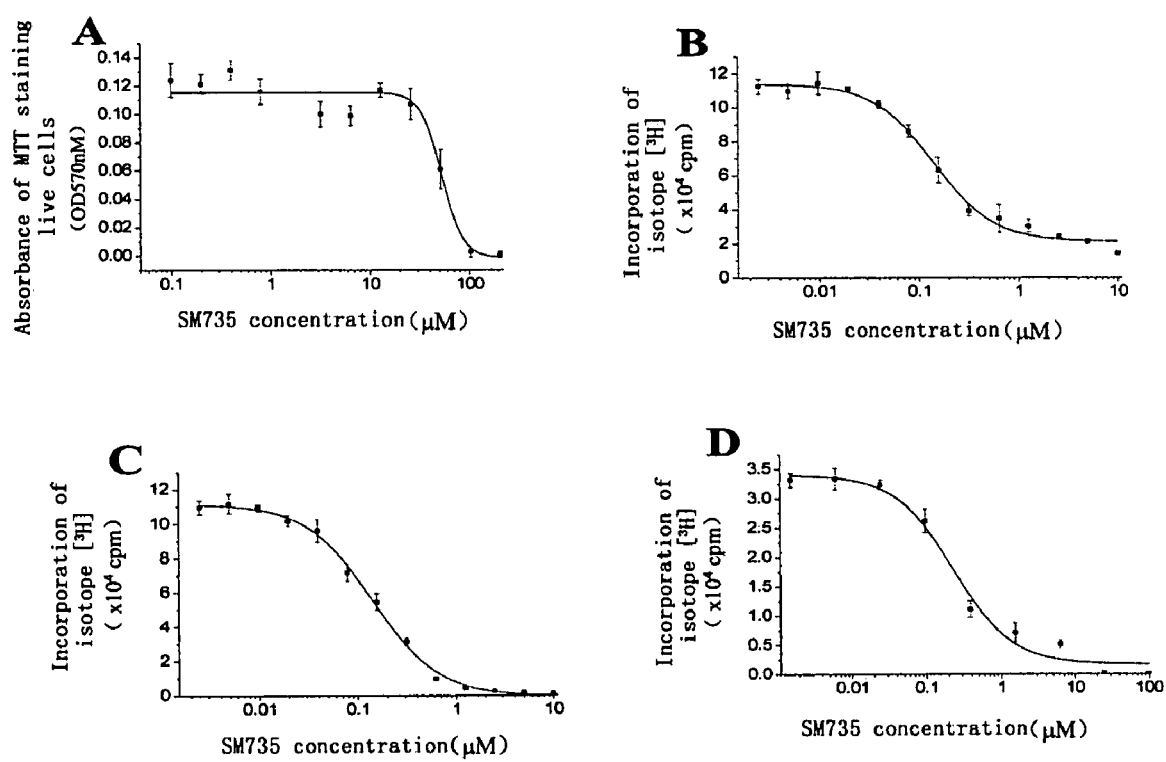
FIG. 1 illustrates the effect of the compound according to the present invention on the non-specific lymphocyte toxicity, the inhibitory effect on the T cell proliferation induced by ConA, the inhibitory effect on the B cell proliferation induced by LPS, and the inhibitory effect on lymphocyte proliferation induced by alloantigen in mixed lymphocyte culture.

Hereinafter, the present invention will be explained detailedly with reference to the examples, but these examples are not construed to be the limit of the present invention.

In the following examples, the artemisinin nucleus is represented by Q:

(Q)

wherein, the ripple line ( ～ ) represents β substitute or/and α substitute;
the solid line ( ▬ ) represents β substitute;
the dash line ( ┈┈ ) represents α substitute.

PREPARATION EXAMPLES

Preparation Example 1

Preparation of methyl 4-(12β-artemisininoxy)phenyl acetate (compound 1)

(compound 1)

Q—O—⟨phenyl⟩—CH$_2$COOMe

Acetyl dihydroartemisinin and methyl 4-hydroxyphenylacetate were dissolved in dichloromethane, and trifluoroacetic acid was added dropwise. After the reaction was finished, some conventional processes was carried out. Separation was carried out with silica gel column chromatography, and then recrystallization was performed to obtain white crystallized product (compound 1) with a melting point of 108-112° C.
Elemental analysis ($C_{24}H_{32}O_7$):
Calculated values: C, 66.65; H, 7.45.
Measured values: C, 67.03; H, 7.21.

Preparation Example 2

Preparation of 4-(12β-artemisininoxy)phenyl acetic acid (compound 2)

(compound 2)

Q—O—⟨phenyl⟩—CH$_2$COOH

The obtained compound of preparation example 1 was hydrolyzed in KOH/$C_2H_5OH$ solution, then the raw product was recrystallized to obtain a white crystallized compound (compound 2) with a melting point of 154-156° C.
Elemental analysis ($C_{23}H_{30}O_7$):
Calculated values: C, 66.01; H, 7.23.
Measured values: C, 65.95; H, 7.29.

Preparation Example 3

Preparation of 3-(12β-artemisininoxy)phenoxy succinic acid (compound 3)

(compound 3)

Q—O—⟨phenyl⟩—O—C(=O)—CH$_2$—CH$_2$—C(=O)—OH

3-Hydroxy phenyl-dihydroartemisinin ether was reacted with succinic anhydride. and a white amorphous solid compound (compound 3) was obtained by silica gel column chromatography.
Elemental analysis ($C_{25}H_{32}O_9 \cdot \tfrac{1}{2}H_2O$):
Calculated values: C, 61.84; H, 6.85.
Measured values: C, 62.09; H, 6.86.

Preparation Example 4

Preparation of dimethylaminoethyl-[4-(12β-artemisininoxy)phenoxy] acetate (compound 4)

(compound 4)

Q—O—⟨phenyl⟩—OCH$_2$COOCH$_2$CH$_2$NMe$_2$

Condensation of 4-carboxy methoxy phenyl-dihydroartemisinin ether and N,N-dimethylethanolamine was carried out to obtain the compound 4.
Elemental analysis ($C_{27}H_{39}NO_8$):
Calculated values: C, 64.14; H, 7.77; N, 2.77.
Measured values: C, 64.30; H, 7.79; N, 2.65.

Preparation Example 5

Preparation of ethyl-[4-(12β-artemisininoxy)benzoyl] aminoacetate (compound 5)

(compound 5)

Q—O—⟨phenyl⟩—CONHCH$_2$COOC$_2$H$_5$

Condensation of 4-carboxylphenyl-dihydroartemisinin ether and ethylglycinate was carried out to obtain the compound 5.

Elemental analysis ($C_{26}H_{35}NO_8$):
Calculated values: C, 63.78; H, 7.21; N, 2.96.
Measured values: C, 64.04; H, 7.26; N, 3.30.

Preparation Example 6

Preparation of 4-[1-(12β-artemisininoxy)ethyl]-phenoxy-acetate (compound 6)

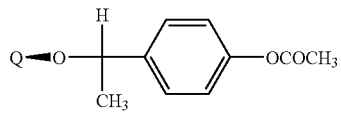

(compound 6)

Condensation of dihydroartemisinin and 4-acetoxy-α-methylbenzylalcohol were carried out to obtain the compound 6.
Elemental analysis ($C_{25}H_{34}O_7$):
Calculated values: C, 67.24; H, 7.67.
Measured values: C, 67.14; H, 7.61.

Preparation Example 7

Preparation of [4-1-(12β-artemisininoxy)ethyl]-phenol (compound 7)

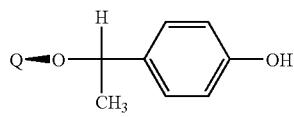

(compound 7)

The compound 6 obtained from preparation example 6 was hydrolyzed in a basic solution to obtain the compound 7.
Elemental analysis ($C_{23}H_{32}O_6$):
Calculated values: C, 68.29; H, 7.97.
Measured values: C, 68.23; H, 8.27.

Preparation Example 8

Preparation of ethyl 4-[1-(12β-artemisininoxy)-ethyl]-phenoxy acetate (compound 8)

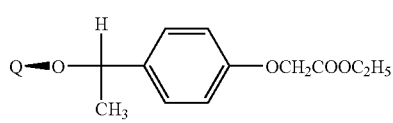

(compound 8)

The compound 7 obtained from preparation example 7 was reacted with ethyl chloroacetate to obtain the compound 8.
Elemental analysis ($C_{27}H_{38}O_8$):
Calculated values: C, 66.10; H, 7.81
Measured values: C, 65.91; H, 8.17.

Preparation Example 9

Preparation of 4-[1-(12β-artemisininoxy)-ethyl]-phenoxy acetic acid (compound 9)

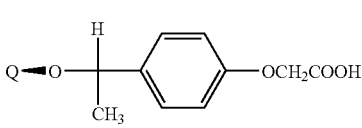

(compound 9)

The compound obtained from preparation example 8 was hydrolyzed in a basic solution to obtain the compound 9.
Elemental analysis ($C_{25}H_{34}O_8$):
Calculated values: C, 64.92; H, 7.41.
Measured values: C, 64.66; H, 7.50.

Preparation Example 10

Preparation of 4-hydroxy-(12β-artemisininoxy)benzylnitrile (compound 10)

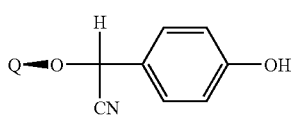

(compound 10)

Condensation of dihydroartemisinin and 4-acetoxy-α-cyanobenzylalcohol and following basic hydrolysis gave the compound 10.
Elemental analysis ($C_{23}H_{29}NO_6$):
Calculated values: C, 66.49; H, 7.04; N, 3.37.
Measured values: C, 66.53; H, 7.04; N, 3.16.

Preparation Example 11

Preparation of 3-hydroxy-(12β-artemisininoxy)benzylnitrile (compound 11)

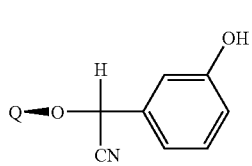

(compound 11)

Condensation of dihydroartemisinin and 3-acetoxy-α-cyanobenzylalcohol and following basic hydrolysis gave the compound 11.
Elemental analysis ($C_{23}H_{29}NO_6$):
Calculated values: C, 66.49; H, 7.04; N, 3.37.
Measured values: C, 66.38; H, 6.84; N, 3.01.

Preparation Example 12

Preparation of (S) 2-ethoxy-carbonyl-methoxy-(12β-artemisininoxy)-benzylnitrile (compound 12) and (R) 2-ethoxy-carbonyl-methoxy-(12β-artemisininoxy)-benzylnitrile (compound 13)

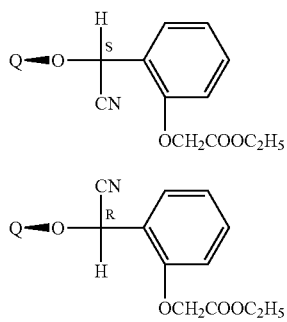

(compound 12)

(compound 13)

Condensation of dihydroartemisinin and 2-ethoxy carbonyl methoxy (α-cyano) benzylalcohol was carried out. When the reaction was completed, conventional process was carried out and separation is performed with silica gel column chromatography.

The first fraction was (S)-2-ethoxy-carbonyl-methoxy-(12β-artemisininoxy)-benzylnitrile, a white crystal with a melting point of 70-71° C.

Elemental analysis: ($C_{27}H_{35}NO_8$)
Calculated values: C, 64.65; H, 7.03; N, 2.79.
Measured values: C, 64.63; H, 7.33; N, 2.85.

The second fraction was (R) 2-Ethoxy-carbonyl-methoxy-(12β-artemisininoxy)-benzylnitrile, a white crystal with a melting point of 88-90° C.

Elemental analysis: ($C_{27}H_{35}NO_8$)
Calculated values: C, 64.65; H, 7.03; N, 2.79.
Measured values: C, 65.08; H, 7.33; N, 2.71.

Preparation Example 13

Preparation of (S)-2-carboxy-methoxy-(12β-artemisininoxy)-benzylnitrile (compound 14)

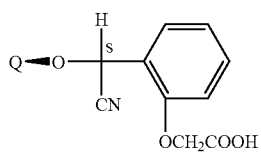

(compound 14)

(S)-2-ethoxy-carbonyl-methoxy-(12β-artemisininoxy)-benzylnitrile obtained in preparation example 12 was hydrolyzed in a basic solution to obtain a white crystallized compound 14 with a melting point of 143-144° C.

Elemental analysis ($C_{25}H_{31}NO_8$):
Calculated values: C, 63.41; H, 6.60; N, 2.96.
Measured values: C, 63.27; H, 6.52; N, 2.97.

Preparation Example 14

Preparation of 2-bromo-5-hydroxy-[12β-artemisininoxy]-benzylnitrile (compound 15)

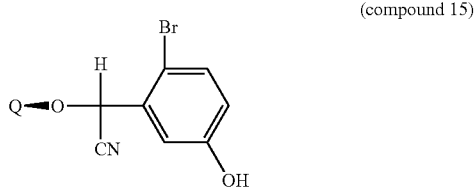

(compound 15)

Dihydroartemisinin and 2-bromo-5-acetoxy (α-cyano) benzylalcohol were used as raw materials, acidic condensation and basic hydrolysis were carried out to obtain a white crystallized compound (compound 15) with a melting point of 90-92° C.

Elemental analysis ($C_{23}H_{28}BrNO_6$):
Calculated values: C, 55.88; H, 5.71; N, 2.83.
Measured values: C, 55.52; H, 5.76; N, 2.82.

Preparation Example 15

Preparation of methyl 4-fluoro-(12β-artemisininoxy)-phenyl acetate (compound 16)

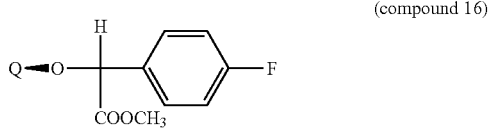

(compound 16)

The condensation of dihydroartemisinin and 4-fluoro (α-ethoxycarbonyl) benzylalcohol was carried out to obtain the compound 16.

Elemental analysis ($C_{24}H_{31}F O_7$):
Calculated values: C, 63.99; H, 6.93.
Measured values: C, 64.29; H, 6.98.

Preparation Example 16

Preparation of ethyl 4-bromo-(12β-artemisininoxy)-phenyl acetate (compound 17)

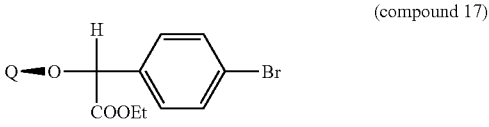

(compound 17)

Condensation of dihydroartemisinin and 4-bromo (α-ethoxycarbonyl) benzylalcohol was carried out to obtain the compound 17.

Elemental analysis ($C_{25}H_{33}BrO_7$):
Calculated values: C, 57.15; H, 6.33.
Measured values: C, 56.87; H, 6.16.

Preparation Example 17

Preparation of methyl (S)-(12β-artemisininoxy)-α-naphthyl acetate (compound 18) and methyl (R)-(12β-artemisininoxy)-α-naphthyl acetate (compound 19)

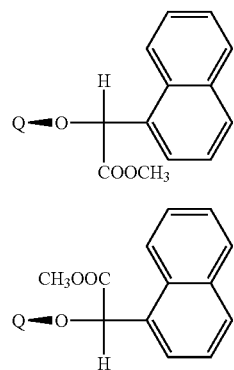

(compound 18)

(compound 19)

The condensation of dihydroartemisinin and α-methyl formate-yl menaphthyl-ol-1 was carried out and separation is performed with column chromatography to obtain the two compounds 18 and 19.

methyl (S)-(12β-artemisininoxy)-α-naphthyl acetate, an amorphous solid.
Elemental analysis ($C_{28}H_{34}O_7$):
Calculated values: C, 69.69; H, 7.10.
Measured values: C, 69.72; H, 7.17.

methyl (R)-(12β-artemisininoxy)-α-naphthyl acetate, an amorphous solid.
Elemental analysis ($C_{28}H_{34}O_7$):
Calculated values: C, 69.69; H, 7.10.
Measured values: C, 70.06; H, 6.97.

Preparation Example 18

Preparation of (S)-(12β-artemisininoxy)-α-naphthyl acetic acid (compound 20)

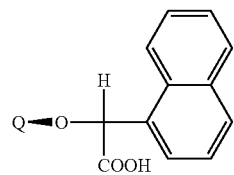

(compound 20)

Basic hydrolysis was performed for the compound methyl (S)-(12β-artemisininoxy)-α-naphthyl acetate obtained in preparation example 17 to obtain the amorphous solid compound 18.
Elemental analysis ($C_{27}H_{32}O_7$):
Calculated values: C, 69.21; H, 6.88.
Measured values: C, 69.29; H, 6.90.

Preparation Example 19

Preparation of methyl 2-[4-(12β-artemisininoxy)phenyl] propionate (compound 21)

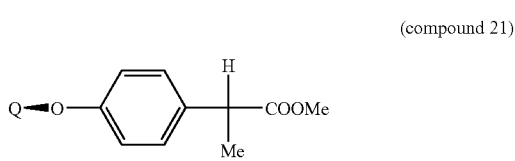

(compound 21)

Condensation of acetyl dihydroartemisinin and methyl 2-(4-hydroxyphenyl)isopropionate was carried out, and conventional process was carried out and separation was performed with silica gel column chromatography to obtain a colorless oily compound 21.
Elemental analysis ($C_{25}H_{34}O_7$):
Calculated values: C, 67.24; H, 7.67.
Measured values: C, 67.05; H, 7.82.

Preparation Example 20

Preparation of 2-[4-(12β-artemisininoxy)phenyl] propanoic acid (compound 22)

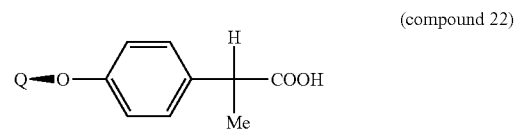

(compound 22)

Basic hydrolysis of the compound of preparation example 19 and recrystallization gave white crystallized compound 22 with a melting point of 152-154° C.
Elemental analysis ($C_{24}H_{32}O_7$):
Calculated values: C, 66.65; H, 7.46.
Measured values: C, 66.63; H, 7.53.

Preparation Example 21

Preparation of o-methoxy-phenyl 2-[4-(12β-artemisininoxy)phenyl] propionate (compound 23)

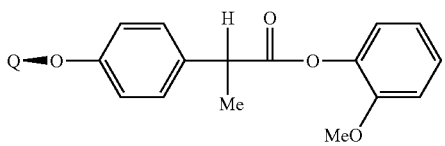

(compound 23)

Condensation of the compound obtained from the preparation example 20 and 2-methoxyphenol was carried out to obtain the compound 23, which was a white amorphous solid.
Elemental analysis ($C_{31}H_{38}O_8$):
Calculated values: C, 69.13; H, 7.11.
Measured values: C, 69.08; H, 7.00.

Preparation Example 22

Preparation of ethyl 2-[4-(12β-artemisininoxy)phenoxy] propionate (compound 24)

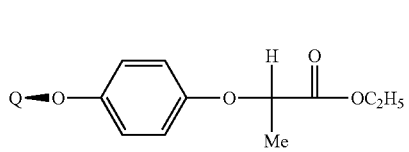
(compound 24)

Condensation of acetyl dihydroartemisinin and ethyl 2-(4-hydroxyphenoxy) propionte was carried out, and after the reaction was completed, conventional processes and separation with silica gel column chromatography were performed to obtain the colorless oily compound 24.

Elemental analysis ($C_{26}H_{36}O_8$):
Calculated values: C, 65.53; H, 7.61.
Measured values: C, 65.46; H, 7.66.

Preparation Example 23

Preparation of 2-[4-(12β-artemisininoxy)phenoxy] propanoic acid (compound 25)

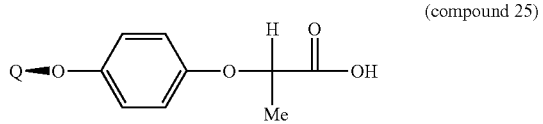
(compound 25)

The compound of preparation example 22 was hydrolyzed in a basic solution to obtain the white amorphous compound 25.

Elemental analysis ($C_{24}H_{32}O_8$):
Calculated values: C, 64.27; H, 7.19.
Measured values: C, 64.25; H, 7.40.

Preparation Example 24

Preparation of o-methoxy-phenyl 2-[4-(12β-artemisininoxy)phenoxy] propionate (compound 26)

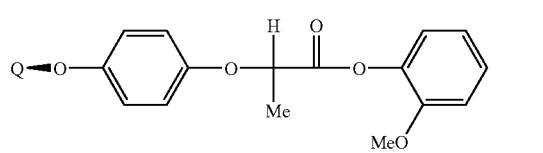
(compound 26)

The aromatic esterification of carboxyl group of 2-[4-(12β-artemisininoxy)phenoxy] propanoic acid was carried out to obtain the compound 26 which was a white crystal with a melting point of 142-144° C.

Elemental analysis ($C_{31}H_{38}O_9$):
Calculated values: C, 67.13; H, 6.91.
Measured values: C, 67.09; H, 6.92.

Preparation Example 25

Preparation of o-methoxy-phenyl 2-[3-(12β-Artemisininoxy)phenoxy] propionate (compound 27)

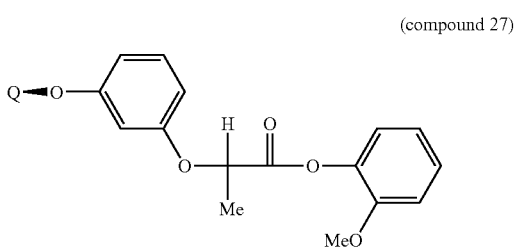
(compound 27)

The aromatic esterification of carboxyl group of 2-[3-(12β-artemisininoxy)phenoxy] propanoic acid was carried out to obtain the compound 27 which was a white amorphous solid.

Elemental analysis ($C_{31}H_{38}O_9$):
Calculated values: C, 67.13; H, 6.91.
Measured values: C, 67.12; H, 7.04.

Preparation Example 26

Preparation of ethyl 2-[3-(12α-artemisininoxy)phenoxy] propionate (compound 28)

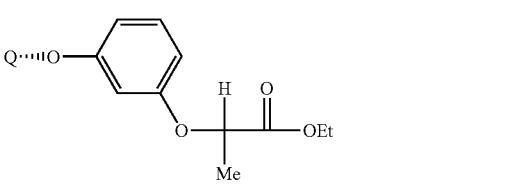
(compound 28)

Condensation of acetyl dihydroartemisinin and ethyl 2-(3-hydroxy phenoxy)propionate was carried out, and after the reaction was completed, conventional process and separation with silica gel column chromatography were carried out to obtain the colorless oily compound 28.

Elemental analysis ($C_{26}H_{36}O_8$):
Calculated values: C, 65.53; H, 7.61.
Measured values: C, 65.17; H, 7.76.

Preparation Example 27

Preparation of 2-[3-(12α-artemisininoxy)phenoxy] propanoic acid (compound 29)

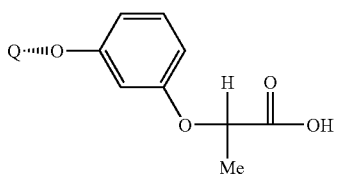
(compound 29)

The compound of preparation example 26 was hydrolyzed in a basic solution to obtain the white amorphous solid compound 29.

Elemental analysis ($C_{24}H_{32}O_8$):
Calculated values: C, 64.27; H, 7.19.
Measured values: C, 64.42; H, 7.50.

Preparation Example 28

Preparation of o-methoxy-phenyl 2-[3-(12α-artemisininoxy)phenoxy] propionate (compound 30)

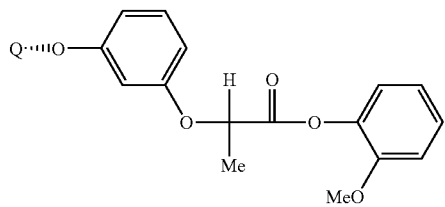
(compound 30)

The free acid obtained from the preparation example 27 was esterified to obtain the white amorphous solid compound 30.

Elemental analysis ($C_{31}H_{38}O_9$):
Calculated values: C, 67.13; H, 6.91.
Measured values: C, 67.52; H, 7.33.

Preparation Example 29

Preparation of ethyl 2-[3-(12β-artemisininoxy)benzyloxy] propionate (compound 31) and ethyl 2-[3-(12α-artemisininoxy)benzyloxy] propionate (compound 32)

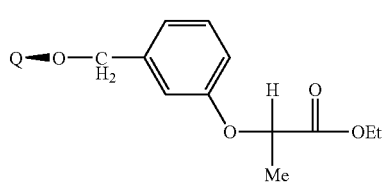
(compound 31)

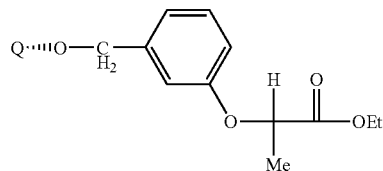
(compound 32)

Condensation of dihydroartemisinin and ethyl 2-(3-hydroxymethyl phenoxy)propionate was carried out, and conventional process and separation with silica gel column chromatography were carried out to obtain two colorless oily compounds 31 and 32.

Elemental analysis ($C_{27}H_{38}O_8$):
Calculated values: C, 66.10; H, 7.81.
(β type) Measured values: C, 66.31; H, 7.67.
(α type) Measured values: C, 66.15; H, 7.91.

Preparation Example 30

Preparation of 2-[3-(12β-artemisininoxy)benzyloxy] propanoic acid (compound 33) and 2-[3-(12α-artemisininoxy)benzyloxy] propanoic acid (compound 34)

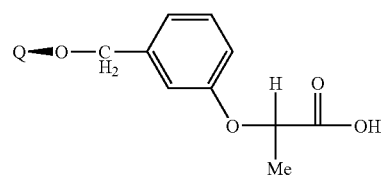
(compound 33)

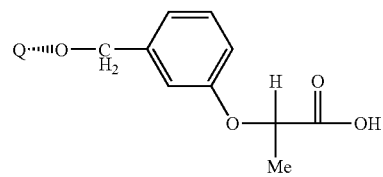
(compound 34)

The compounds obtained from the preparation example 29 were hydrolyzed in a basic solution to obtain two white amorphous solid compounds 33 and 34.

Elemental analysis ($C_{25}H_{34}O_8$):
Calculated values: C, 64.92; H, 7.41.
(β type) Measured values: C, 64.64; H, 7.61.
(α type) Measured values: C, 66.76; H, 7.66.

Preparation Example 31

Preparation of o-methoxy-phenyl 2-[3-(12α-artemisininoxy)benzyloxy] propionate (compound 35)

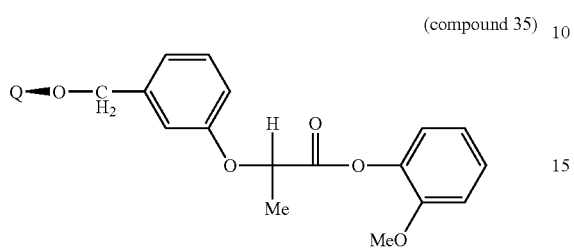
(compound 35)

The aromatic esterification of carboxyl group of the β type compound obtained from the preparation example 30 was carried out to obtain the colorless oily compound 35.

Elemental analysis ($C_{32}H_{40}O_9$):
Calculated values: C, 67.59; H, 7.09.
Measured values: C, 67.54; H, 7.17.

Preparation Example 32

Preparation of ethyl 2-[4-(12β-artemisininoxy)benzyloxy] propionate (compound 36) and ethyl 2-[4-(12α-artemisininoxy)benzyloxy] propionate (compound 37)

(compound 36)

(compound 37)

Condensation of dihydroartemisinin and ethyl 2-(4-hydroxymethyl phenoxy)propionate was carried out, and conventional process and separation with silica gel column chromatography were performed to obtain two colorless oily compounds 36 and 37.

Elemental analysis ($C_{27}H_{38}O_8$):
Calculated values: C, 66.10; H, 7.81.
(β type) Measured values: C, 66.03; H, 7.70.
(α type) Measured values: C, 66.18; H, 7.49.

Preparation Example 33

Preparation of 2-[4-(12β-artemisininoxy)benzyloxy] propanoic acid (compound 38) and 2-[4-(12α-artemisininoxy)benzyloxy] propanoic acid (compound 39)

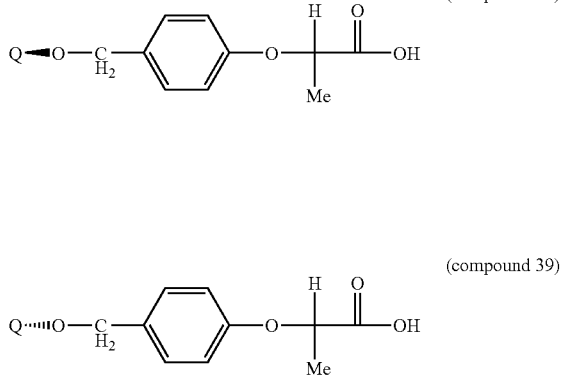
(compound 38)

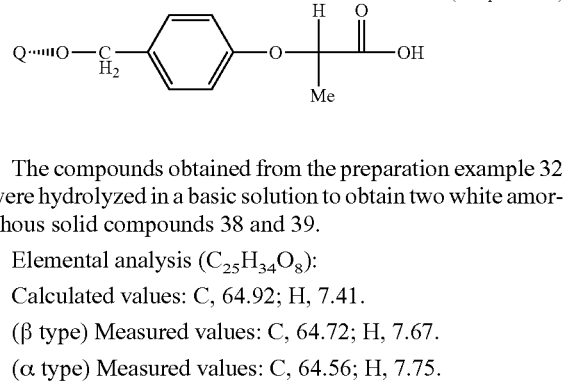
(compound 39)

The compounds obtained from the preparation example 32 were hydrolyzed in a basic solution to obtain two white amorphous solid compounds 38 and 39.

Elemental analysis ($C_{25}H_{34}O_8$):
Calculated values: C, 64.92; H, 7.41.
(β type) Measured values: C, 64.72; H, 7.67.
(α type) Measured values: C, 64.56; H, 7.75.

Preparation Example 34 o-methoxy-phenyl 2-[4-(12β-artemisininoxy)benzyloxy] propionate (compound 40)

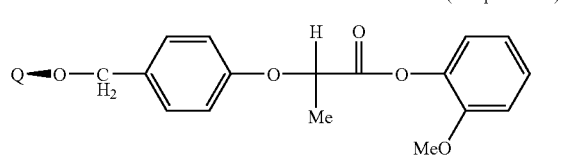
(compound 40)

The aromatic esterification of carboxyl group of the β type compound obtained from the preparation example 33 was carried out to obtain the colorless oily compound 40.

Elemental analysis ($C_{32}H_{40}O_9$):
Calculated values: C, 67.59; H, 7.09.
Measured values: C, 67.55; H, 7.21.

Preparation Example 35

Preparation of ethyl 4-[1-(12β-artemisininoxy)ethyl] phenoxy propionate (compound 41) and 4-ethoxy carbonyl-(α-methyl)methenyloxy (α-methyl)benzyl-11-α-methyl dihydroartemisinin ether (compound 42)

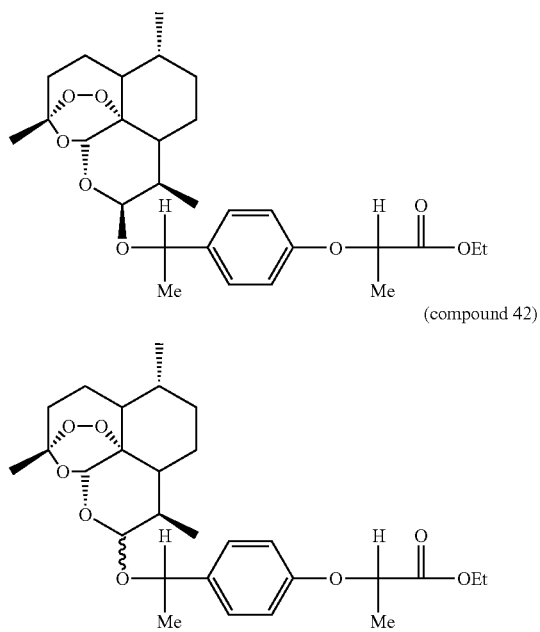

(compound 41)

(compound 42)

Condensation of dihydroartemisinin and ethyl 2-[4-(α-methyl)hydroxylmethyl phenoxy] propionate was carried out, and conventional process and the separation with silica gel column chromatography are performed to obtain two colorless oily compounds 41 and 42.

Elemental analysis ($C_{28}H_{40}O_8$):
Calculated values: C, 66.65; H, 7.99.
(11-β) Measured values: C, 66.60; H, 7.88.
(11-α) Measured values: C, 66.77; H, 8.11.

Preparation Example 36

Preparation of ethyl 4-(12β-artemisininoxy)-phenoxy acetate (compound 43)

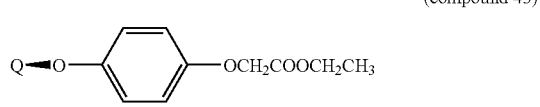

(compound 43)

4-(12β-artemisininoxy)-phenoxy acetic acid was esterified to obtain the white amorphous solid compound 43.

Elemental analysis ($C_{25}H_{34}O_8$):
Calculated values: C, 64.92; H, 7.41.
Measured values: C, 64.62; H, 7.40.

Preparation Example 37

Preparation of a tablet containing 2-[4-(12β-artemisininoxy)phenyl] propanoic acid
The formula is as follows: the content of each component was measured by weight percent

| | |
|---|---|
| 2-[4-(12β-artemisininoxy)phenyl] propanoic acid | 35% |
| starch | 25% |
| microcrystalline cellulose | 30% |
| sodium carboxymethyl starch | 3% |
| starch paste (10%) | 6% |
| magnesium stearate | 1% |

The active component was pulverized, and screened with 100 mesh sieve; after mixed homogeneously with microcrystalline cellulose, starch and sodium carboxymethyl starch, a proper amount of 10% starch paste was added to prepare the damp mass; after granulation is carried out with 20 mesh sieve, the material was dried at 60□, and granulae are processed; then the lubricant magnesium stearate was added into and mixed uniformly; tabletting was performed to obtain the final product.

Preparation Example 38

Preparation of a tablet containing 3-(12β-artemisininoxy)phenoxy succinic acid

The formula was as follows: all the content of each component was measured by weight percent

| | |
|---|---|
| 3-(12β-artemisininoxy)phenoxy succinic acid | 30% |
| microcrystalline cellulose | 65% |
| crosslinked polyvidone | 1.5% |
| micronized polyethylene glycol 4000 | 3% |
| micronized silica gel | 0.5% |

The active component was pulverized, and screened with 100 mesh sieve; after homogeneously mixed with the filler microcrystalline cellulose, the disintegrating agent crosslinked polyvidone, the lubricant micronized polyethylene glycol 4000, and the glidant micronized silica gel, tabletting was performed directly to obtain the final product.

Preparation Example 39

Preparation of an Enteric Coated Tablet Containing o-methoxy-phenyl 2-[4-(12β-artemisininoxy)phenoxy] propionate The formula was as follows: the content of each component was measured by weight percent

| | |
|---|---|
| o-methoxy-phenyl 2-[4-(12β-artemisininoxy) phenoxy propionate | 35% |
| pregelating starch | 20% |
| microcrystalline cellulose | 35% |
| crosslinking sodium carboxymethyl cellulose | 4% |

| | |
|---|---|
| aqueous solution of polyvidone (8%) | 4% |
| talc powder | 2% |

The active component was pulverized, and screened with 100 mesh sieve; after homogeneously mixed with microcrystalline cellulose, pregelating starch and crosslinking sodium carboxymethyl cellulose, a proper amount of 8% aqueous solution of polyvidone was added to prepare the damp mass; after granulation is carried out with 20 mesh sieve, the material was dried at 60□, and granulae are processed; then the lubricant talc power was added into and mixed uniformly; tabletting was performed to obtain the core.

Subsequently, the core was coated with 3% hydroxypropyl emthylcellulose (E5) alchol aqueous solution to form an isolation coating until the weight was increased by 8%; then Eudragit L30D was coated to form a enteric coating until the weight was increased by 10%, thereby the final product was obtained.

Preparation Example 40

Preparation of a hard capsule containing methyl 4-(12β-artemisininoxy)phenyl acetate The formula was as follows: the content of each component was measured by weight percent

| | |
|---|---|
| methyl 4-(12β-artemisininoxy) phenyl acetate | 50% |
| pregelating starch | 40% |
| talc powder | 9% |
| micronized silica gel | 1% |

The active component and the adjuvants are homogeneously mixed and packed into empty capsule to obtain the final product.

Preparation Example 41

Preparation of a soft capsule containing ethyl 4-(12β-artemisininoxy)-phenoxy acetate The formula is as follows: the content of each component was measured by weight percent

| | |
|---|---|
| ethyl 4-(12β-artemisininoxy)-phenoxy acetate | 45% |
| polyethylene glycol 400-1000 | 30% |
| suspending agent (10~30% oil-wax mixture) | 25% |

The active component was pulverized and sieved, and other components were added and mixed thoroughly, then the soft capsule are prepared in a pelletizing machine.

Preparation Example 42

Preparation of a gel containing methyl 2-[4-(12β-artemisininoxy)phenyl] propionate The formula was as follows: the content of each component was measured by weight percent

| | |
|---|---|
| methyl 2-[4-(12β-artemisininoxy) phenyl] propionate | 5% |
| crosslinking sodium polyacrylate | 2% |
| polyethylene glycol 4000 | 8% |
| glycerol | 10% |
| Benzalkonium bromide | 1% |
| water | 74% |

After polyethylene glycol 4000 and glycerol were heated to be molten and merged, the active component was added after being pulverized and sieved, and mixed homogenously; after crosslinking sodium polyacrylate was added into a proper amount of water (60° C.) and stirred thoroughly, the matrix was mixed homogenouly with the active component, polyethylene glycol 4000 and glycerol, then sufficient water was added to obtain the final product.

Preparation Example 43

Preparation of a suppository containing o-methoxy-phenyl 2-[3-(12β-artemisininoxy)phenoxy] propionate The formula was as follows: the content of each component was measured by weight percent

| | |
|---|---|
| o-methoxy-phenyl 2-[3-(12β-artemisininoxy) phenoxyl] propionate | 15% |
| polyoxyethylene(40) monostearate | 85% |

The active component was pulverized and sieved, a small amount of molten matrix was added, after being ground and mixed sufficiently, the mixture was mixed with other molten matrix, and injected into suppository mold while maintaining the temperature.

Preparation Example 44

Preparation of a cream containing ethyl-[4-(12β-artemisininoxy)benzoyl] aminoacetate The formula was as follows: the content of each component was measured by weight percent

| | |
|---|---|
| ethyl-[4-(12β-artemisininoxy) benzoyl] aminoacetate | 2.5% |
| glyceryl monostearate | 8.5% |
| stearic acid | 15% |
| white vaseline | 10% |
| glycerol | 8% |
| Tween-80 | 3% |
| water | 53% |

The active component was dissolved in a small amount of acetone, then glyceryl monostearate, stearic acid and white vaseline were added and heated together to be molten while maintaining the temperature at 80° C. Tween-80, glycerin and water were also heated to 80° C. and added into the above oil phase slowly, the mixture was stirred along a same direction to obtain a white fine cream.

Preparation Example 45

Preparation of a patch containing dimethylaminoethyl-[4-(12β-artemisininoxy)phenoxy] acetate The formula was as follows: the content of each component was measured by weight percent

| | |
|---|---|
| dimethylaminoethyl-[4-(12β-artemisininoxy)phenoxyl] | 15% |
| acrylic resin | 55% |
| dibutyl sebacate | 25% |
| acetone | 5% |

Acrylic resin used as matrix and plasticizer dibutyl sebacate of the amount as prescribed in the formula were dissolved in suitable amount of acetone and mixed homogenously; then active component dispersed in acetone was added and stirred homogenously while heating gently to obtain a clear solution. The solution was coated on a substrate or antistick layer and dried at 60° C., and the final product was obtained by cutting the substrate according to the desired dose.

Test Example

The inventor carried out the screening and study of in vitro and in vivo immunosuppressive activity of the artemisinin derivative with the following methods (see Modern Pharmacological Experimental Methods, Zhang Juntian ed. Beijing Medical University/Chinese Peking Union Medical University Union Press, published in 1998).

Experimental Materials

Experimental animals: inbred BALB/c and C57BL/6 male mice, 6-8 weeks old.

RPMI-1640 culture solution (purchased from Gibco, pH7.2) with 10% fetal bovine serum (FBS), 100 U/mL penicillin, 100 μg/mL streptomycin, 10 mM HEPES (2-[4-(2-Hydroxy ethyl)-1-piperazinyl] ethanesulfonic acid), and 50 μM 2-ME (2-Mercaptoethanol).

Stimulator: Concanavalin A (ConA), Lipopolysaccharide (LPS, from *Escherichia Coli* 055:B5), diluted with RPMI-1640 medium to suitable concentration before using.

Experimental Methods

A. Lymphocytotoxicity Test

1. BALB/c mice were killed by cervical dislocation, and their spleens were removed aseptically. A single spleen cell suspension was prepared and cell debris and clumps were removed. Erythrocytes were lysed with Tris-buffered ammonium chloride (0.155 M NH4Cl and 16.5 M Tris, pH 7.2). Mononuclear cells were washed and resuspended in RPMI-1640 medium (containing 10% FBS).

2. 80 μL cell suspension, 40 μL testing sample, 40 μL medium containing 10% FBS were added into 96 well plate; for the control group, 80 μL medium was added the total volume was 160 μL, and blank control group was set.

3. After incubated in 5% $CO_2$ incubator at 37° C. for 48 hours, 16 μL MTT (5 mg/mL) reagent was added into each well 6-7 hours before the termination of the incubation.

4. When the incubation is terminated, 80 μL MTT dissolving solution (10% SDS, 50% dimethylformamide; pH7.2) was added into each well, after placed in incubator for 6-7 hours, OD values was measured with a microplate reader at 570 nm.

B. Lymphocyte Proliferation Test

1. BALB/c mice were killed by cervical dislocation, their spleens were removed aseptically, and a single spleen cell suspension was prepared. The cell concentration was adjusted to $4 \times 10^6$/mL with RPMI-1640 medium containing 10% FBS.

2. 100 μL cell suspension, 50 μL test sample solution, 50 μL concanavalin A (Con A) or lipopolysaccharide (LPS) were added into 96-well plate; for the control group, 50 μL medium containing 10% FBS was added, the total volume was 200 μL.

3. After incubated in 5% $CO_2$ incubator at 37° C. for 48 hours, 0.5 μCi [$^3$H]-thymidine (25 μL/well) was added into each well 7-8 hours before the termination of the incubation.

4. The incubation is terminated, the cells were harvested with a cell harvestor (HARVESTER96®, TOMTEC) on a glass fiber film, scintillation fluid was added, and the incorporation of [$^3$H]-thymidine in the cell DNA was detected with a liquid scintillation counter (MicroBeta Trilux®, PerkinElmer), which indicated the state of cell proliferation.

C. Mixed Lymphocyte Reaction (MLR)

1. C57BL/6 and BALB/c mice were killed by cervical dislocation, their spleens were removed aseptically, and a single spleen cell suspension was prepared. After the red blood cells were removed, the cell concentration was adjusted to $4 \times 10^6$/mL with RPMI-1640 medium containing 10% FBS.

2. The spleen cells of C57BL/6 mice were response cells, and the spleen cells of BALB/c mice (irradiated with Co60, 3000 rads) were stimulator cells, the two kinds of cells were mixed with equal volumes.

3. 100 μL mixed cell suspension, 100 μL test sample were added into a 96-well plate; for the control group, 100 μL medium containing 10% serum was added, and single culture controls of the two kinds of cells were set.

4. Incubated in 5% $CO_2$ incubator at 37° C. for 3, 4 or 5 days. 25 μL $^3$H dilution (i.e. $3.8 \times 10^{10}$ Bq [$^3$H]-thymidine) was added 1 day before the termination of the incubation.

5. The incubation was terminated, the plate was freezed in a −20° C. refrigerator.

6. The cells were harvested with a cell harvestor (HARVESTER96®, TOMTEC) on a glass fiber film, the incorporation of [$^3$H]-thymidine in DNA was detected with a liquid scintillation counter (MicroBeta Trilux®, PerkinElmer), which reflected the state of cell proliferation.

D. Induction and Detection of Cytokine

1. BALB/c mice were killed by cervical dislocation, their spleens were removed aseptically, and a single spleen cell suspension was prepared. After the red blood cells were removed, the cell concentration was adjusted to $5 \times 10^6$/mL with RPMI-1640 medium containing 10% FBS.

2. 1 mL cell suspension, 0.5 mL test sample and 0.5 mL ConA (final concentration 5 μg/mL) or Sac (*Staphylococcus aureus* thallus containing *staphylococcus* protein A) (final concentration 0.01%) were added into 96-well plate; for the control group, 0.5 mL medium containing 10% FBS was added, the final volume was 2 mL.

3. Incubated in 5% $CO_2$ incubator at 37° C. for 24 or 48 hours, the supernatant was collected and freezed in −20° C. refrigerator, the cytokines was to be detected.

4. Production of cytokines was detected with a double antibody sandwich enzyme linked immunosorbent assay (ELISA). TMB was used as substrate of the enzyme reaction, and the OD values was measured with a microplate reader at 450 nm. The production amount of cytokines of the samples was calculated according to the standard curve.

E. Delayed Hypersensitive Response Animal Model (DTH)

1. Each rear paw of BALB/c mice (female, 6-8 weeks old) was sensitized with 20 μL 0.5% DNFB (2,4-dinitrofluorobenzene) on day 0, and was reinforced next day (DNFB was dissolved in an oil agent [acetone:olive oil=4:1]);

2. Inside and outside of left ear of the mice were challenged with 10 μL 0.4% DNFB at day 7-9;

3. The test sample was administrated once 1 hour before challenge by i.p. injection or intragastric adminatration. After 12 hours, administered again;

4. 24-48 hours after challenge, each index was measured.

Note: For BALB/c mice (female, 6-8 weeks old), the concentration of sensitizing agent was 0.7%, the concentration of challenging agent was 0.6%.

F. Production of Anti Sheep Red Blood Cell Specific Antibody of Mouse B Cells

1. Fresh sheep red blood cells (SRBC) were washed 3 times with PBS (pH7.2), and diluted by 1:20;

2. Fresh serum of guinea pig was diluted by 1:10;

3. $2 \times 10^7$/mL of mouse spleen cell suspension was prepared;

4. Each 1 mL of the above three solutions was mixed and incubated at 37° C. for 1.5 hours, then is centrifuged with 2500 rpm×15 min. OD value was measured at 520 nM.

BALB/c mice were sensitized 3 days after administration: the sheep red blood cells were washed 3 times with saline, and the SRBC pressed volume was diluted by a rate of 5%. Each mouse was intraperitoneally injected with 0.2 mL, and dissected to take its spleen 6 days after sensitization. And the production amount of the antibodies was measured.

G Rat Adjuvant-Induced Arthritis Model 60 male SD rats were randomly divided into 5 groups. Inactivated BCG was prepared with sterile liquid paraffin to 10 g/L, and shaken to mix homogenously. Left rear foot pad of the rat was injected with 0.1 mL intracutaneously. The rats were observed for consecutive 28 days. The secondary swelling of paws on the opposite side of the injection site was the indication of arthritis. From day 12, displacement method was used to measure the paw volume below ankle joint every 4 days. Meanwhile, the severity of polyarticular arthritis pathology was scored according to the following standard: 0: no reddish swelling; 1: joint of little toe slightly swelling; 2: joint of toe and sole swelling; 3: paw below ankle joint swelling; 4: the whole paw including ankle joints swelling. The highest score of each rat was 16. The test sample was intraperitoneally injected from 2 days before immunization until 28 days after immunization. The effect of test sample on the induction and preventive/therapeutic treatment of the rat adjuvant-induced arthritis animal model was observed.

Experimental results showed that the lymphocytoxicity of the compound prepared in the examples of the present invention was relatively low, some of which were lower than the cytotoxicity of the control samples artemisinin and artesunate. Meanwhile, all the serial of compounds could significantly inhibit the proliferation response of the T and B lymphocytes induced and initiated by mitogens. The cytotoxic concentration of the compound that reduces cell viability by 50% ($CC_{50}$), the higher the value, the lower the toxicity of some compounds and the inhibitory concentration of the compound that reduces cell proliferation by 50% ($IC_{50}$), the lower the value, the stronger the toxicity for inhibiting the T lymphocyte proliferation response induced by Con A and B lymphocyte proliferation response induced by LPS were listed in the attached table 1. It can be seen that the immunosuppressive activity of some compounds was obviously better than the control samples artemisinin and artesunate. The following table 1 showed the specific experimental results.

TABLE 1

| compound | Lymphocyto-toxicity $CC_{50}$ (M) | Inhibiting activity of T lymphocyte proliferation response induced by ConA $IC_{50}$ (M) | Inhibiting activity of B lymphocyte proliferation response induced by LPS $IC_{50}$ (M) |
|---|---|---|---|
| artemisinine | $2.83 \times 10^{-5}$ | $4.43 \times 10^{-6}$ | $8.96 \times 10^{-6}$ |
| artesunate | $8.60 \times 10^{-5}$ | $3.82 \times 10^{-6}$ | $1.78 \times 10^{-6}$ |
| compound 1 | $8.00 \times 10^{-6}$ | $7.13 \times 10^{-7}$ | $1.79 \times 10^{-7}$ |
| compound 2 | $1.00 \times 10^{-4}$ | $1.18 \times 10^{-5}$ | $1.02 \times 10^{-5}$ |
| compound 3 | $5.27 \times 10^{-5}$ | $3.27 \times 10^{-7}$ | $2.65 \times 10^{-7}$ |
| compound 4 | $2.08 \times 10^{-6}$ | $1.96 \times 10^{-6}$ | $4.96 \times 10^{-8}$ |
| compound 5 | $3.90 \times 10^{-5}$ | $2.53 \times 10^{-6}$ | $1.60 \times 10^{-7}$ |
| compound 21 | $7.80 \times 10^{-6}$ | $6.40 \times 10^{-8}$ | $1.60 \times 10^{-7}$ |
| compound 22 | $5.96 \times 10^{-5}$ | $3.60 \times 10^{-6}$ | $8.60 \times 10^{-6}$ |
| compound 23 | $5.33 \times 10^{-6}$ | $5.27 \times 10^{-7}$ | $9.47 \times 10^{-7}$ |
| compound 24 | $1.76 \times 10^{-5}$ | $2.60 \times 10^{-7}$ | $8.50 \times 10^{-7}$ |
| compound 25 | $2.43 \times 10^{-5}$ | $7.27 \times 10^{-6}$ | $8.60 \times 10^{-7}$ |
| compound 26 | $3.91 \times 10^{-5}$ | $2.33 \times 10^{-6}$ | $2.70 \times 10^{-7}$ |
| compound 27 | $2.99 \times 10^{-6}$ | $4.12 \times 10^{-6}$ | $5.70 \times 10^{-7}$ |
| compound 28 | $2.99 \times 10^{-6}$ | $3.59 \times 10^{-6}$ | $5.60 \times 10^{-7}$ |
| compound 29 | $3.51 \times 10^{-5}$ | $8.60 \times 10^{-6}$ | $7.40 \times 10^{-7}$ |
| compound 30 | $8.23 \times 10^{-6}$ | $5.73 \times 10^{-6}$ | $8.20 \times 10^{-7}$ |

After in vivo administration (intraperitoneal administration), many compounds can significantly inhibit the swelling of mouse ear induced by 2,4-dinitrofluorobenzene (DNFB) and the secretion of specific mouse anti sheep red blood cell antibody caused by sheep red blood cells, this result shows that these compounds have good immunosuppressive activity in the experimental systems in vivo.

Figure 2:
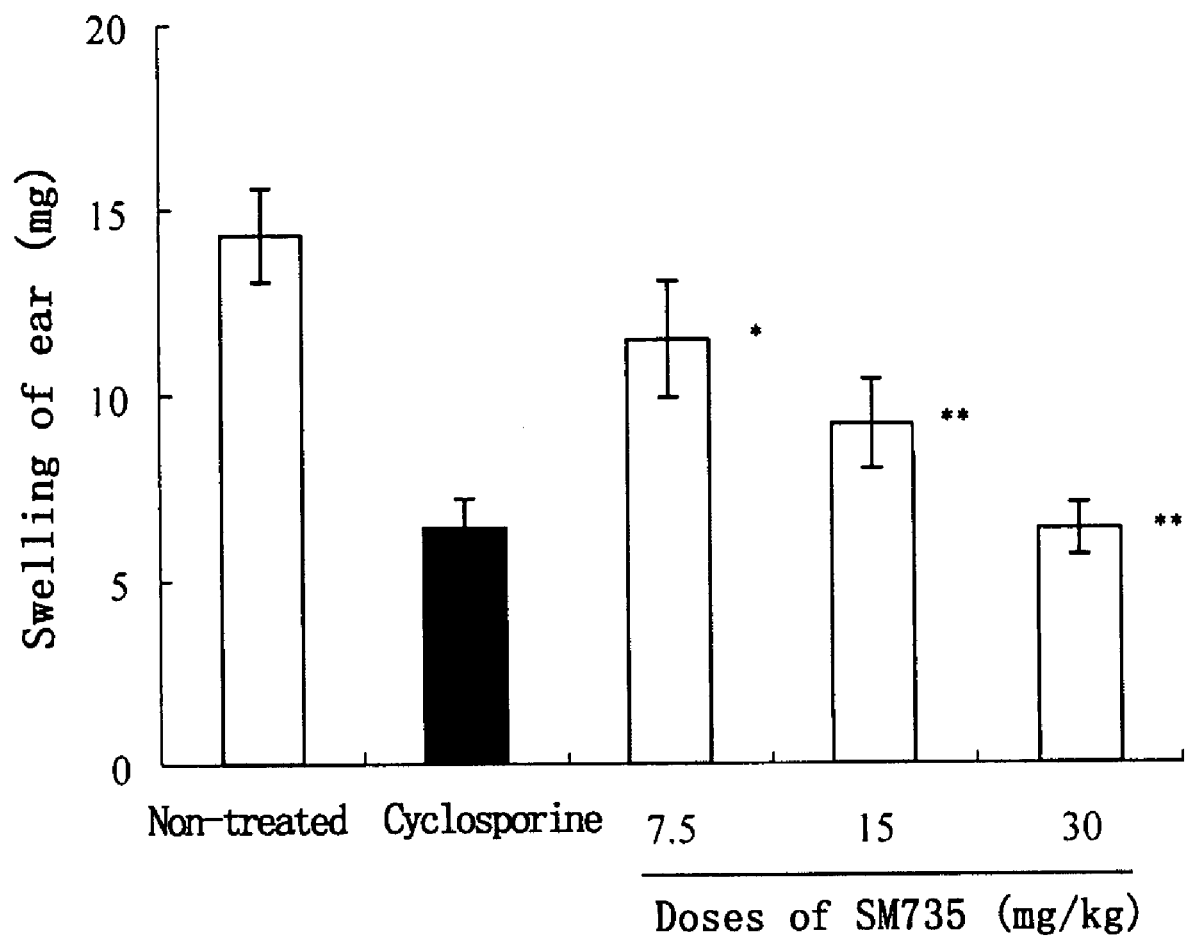
FIG. 2 illustrates the inhibition of the compound according to the present invention on the production of antibody and complement by the mouse B cells (antibody forming cells) when administrated in vivo.
Figure 3:
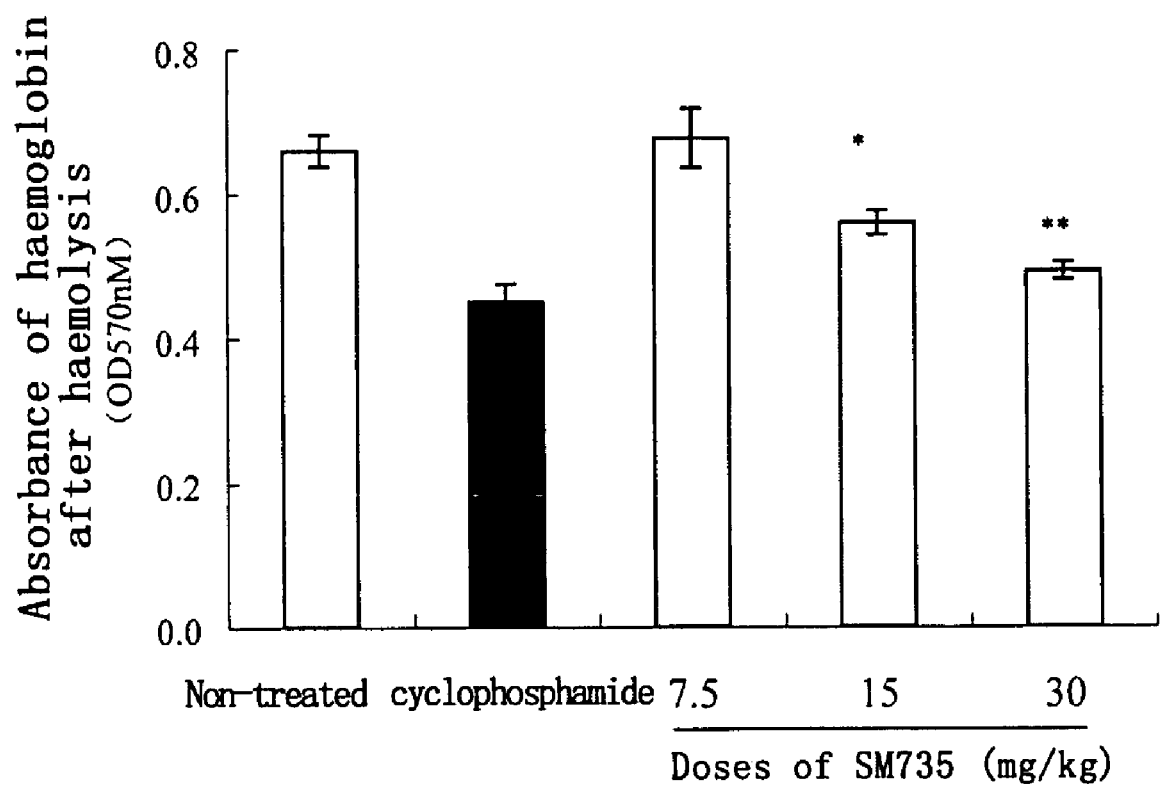
FIG. 3 illustrates the inhibition of the compound of the present invention on the DTH reaction induced by DNFB.

For example, pharmacological test was carried out on 3-succinic acid monoacyl phenyl-dihydroartemisinin ether (β type) (SM735) prepared in the preparation example 3. As shown in FIG. 1(A), the cytotoxicity was detected by MTT method for co-culture of SM735 and BALB/c mouse spleen cells for 48 hours, $CC_{50}$ was 53.1±7.8 μM. As shown in FIG. 1(B), SM735 inhibited the proliferation of spleen cells for 48 hours induced by ConA, $IC_{50}$ was 0.33±0.06 μM. As shown in FIG. 1(C), SM735 inhibited the proliferation of spleen cells for 48 hours induced by LPS, $IC_{50}$ was 0.27±0.02 μM. As shown in FIG. 1(D), SM735 inhibited one way mixed lymphocyte reaction, and its $IC_{50}$ was 0.86±0.18 BALB/c mouse spleen cells and C57BL/6 mouse spleen cells inactivated with mitomycin C were co-cultured for 96 hours, and SM735 was added. Three different experiments showed the same results. All data were showed as mean value ±standard error. The data were calculated by Origin® statistics software after logarithm treatment. Coefficient of correlation were (A) $R^2=0.960$; (B) $R^2=0.993$; (C) $R^2=0.997$; (D) $R^2=0.984$. As shown in FIG. 2, BALB/c mice were sensititized with DNFB on the starting day of the experiment day 0 and day 1 and then challenged on day 9. Cyclosporin A and SM735, and the solvent control were administered on days 7-10 of the experiment for 4 consecutive days. 48 hours after challenging, ear patches were taken, and the degree of swelling is measured, i.e. the volume of left ear patch (treated with DNFB) subtracted the volume of right ear patch (not treated). Data was shown as mean value ±standard error, *P<0.05, **P<0.01, n=10 mice/group. Three independent experiments had the same results. As shown in FIG. 3, BALB/c mice were immunized with sheep red blood cells, the ability of mouse B lymphocyte producing antibody was measured. Each group (6 mice) was administered with solvent control, 25 mg/kg cyclophosphamide or SM735 respectively for consecutive 4 days. Mouse spleen cell suspension, sheep red blood cells and guinea pig complement were co-incubated for half an hour at 37° C. The absorbance of cultural supernatant was measured at 520 nm wavelength to reflect the ability of B lymphocyte producing antibody. Data were shown as mean value ±standard error. *P<0.05, **p<0.01 (two tailed Student's t-test).

Figure 4:
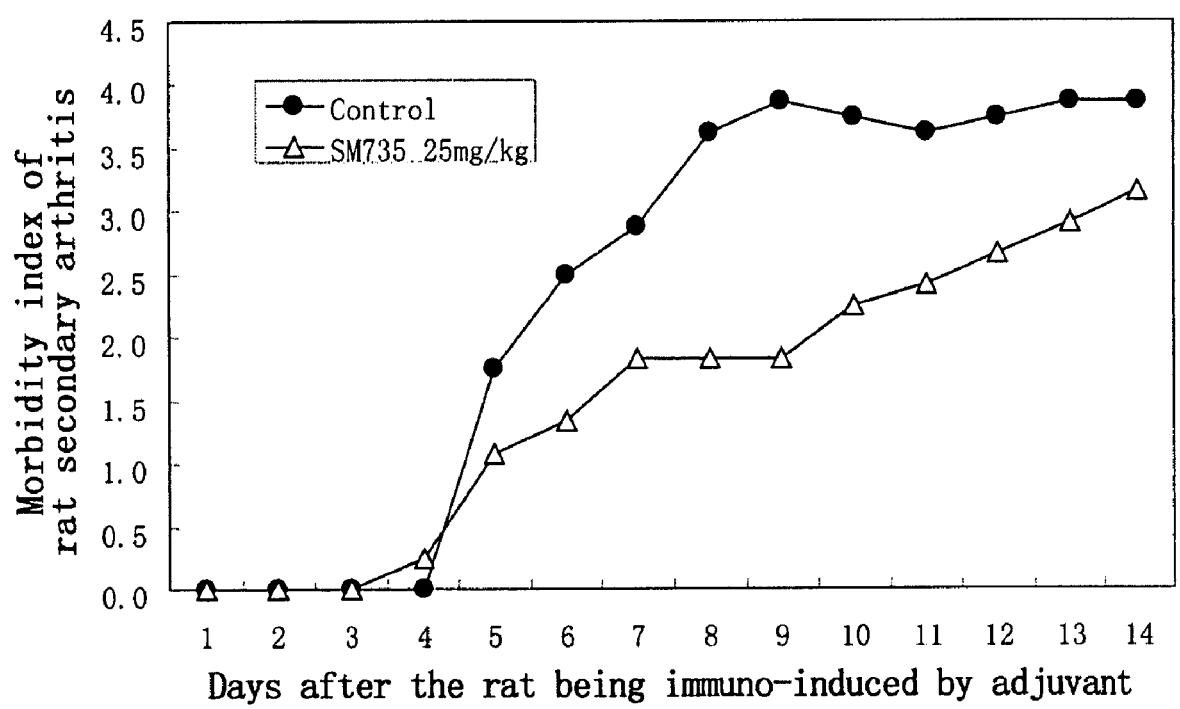
FIG. 4 illustrates the certain preventive and therapeutic effect of the compound of the present invention in rat adjuvant-induced arthritis model.

Experimental results indicated that 3-succinic acid monoacyl phenyl-dihydroartemisinin ether (β type) (SM735) had the following immunosuppressive activities in vivo and in vitro:

1) Non-specific lymphocytotoxicity was very low, $CC_{50}$ value was 53.1±7.8 μM or 27 μg/mL (FIG. 1A);

2) It strongly inhibited T lymphocyte proliferation response induced by ConA, $IC_{50}$ value was 0.33±0.06 μM or 0.13 μg/mL (FIG. 1B);

3) It strongly inhibited B lymphocyte proliferation response induced by LPS, $IC_{50}$ value was 0.27±0.02 μM or 0.12 μg/mL (FIG. 1C);

4) It strongly inhibited proliferation response caused by mixed lymphocyte reaction, $IC_{50}$ value was 0.86±0.18 μM or 2.1 μg/mL (FIG. 1D);

5) It inhibited the secretion of cytokine when lymphocyte was activating. It obviously inhibited the production of TNF-α, especially IL-6 when stimulated with PMA, and this inhibiting activity was dose dependent. It also inhibited the production of IFN-γ and IL-12, two important Th1 type T cell differentiation enhancing factor (the results was shown in Table 2);

6) It inhibited antibody and complement production by mouse B cell (antibody forming cell) when administered in vivo (FIG. 2);

7) It inhibited DTH reaction induced by DNFB (FIG. 3);

8) It had certain preventive and therapeutic effect in rat adjuvant-induced arthritis animal model (FIG. 4).

TABLE 2

Effect of SM735 on cytokine production of activated spleen lymphocytes

| SM735 (Mol/L) | stimulator | production of cytokine (pg/ml) | | |
|---|---|---|---|---|
| | | IL-2 | IFN-γ☐ | |
| — | — | 27 ± 2 | 83 ± 7 | |
| — | ConA | 2321 ± 33 | 1523 ± 22 | |
| $10^{-7}$ | ConA | 2250 ± 77 | 1219 ± 33 ** | |
| $10^{-6}$ | ConA | 2343 ± 154 | 976 ± 18 ** | |
| $10^{-5}$ | ConA | 2053 ± 162 | 322 ± 18 ** | |
| | | IL-12 | IFN-γ☐ | IL-6 |
| — | — | 145 ± 17 | 97 ± 21 | 397 ± 27 |
| — | LPS | 707 ± 8 | 240 ± 13 | 1013 ± 43 |
| $10^{-7}$ | LPS | 592 ± 33 * | 207 ± 13 * | 840 ± 10 ** |
| $10^{-6}$ | LPS | 565 ± 18 ** | 172 ± 2 ** | 792 ± 42 ** |
| $10^{-5}$ | LPS | 292 ± 26 ** | 103 ± 7 ** | 522 ± 1 ** |
| — | PMA + Ion | 699 ± 29 | 844 ± 36 | 3256 ± 176 |
| $10^{-7}$ | PMA + Ion | 586 ± 52 * | 768 ± 6 ** | 2886 ± 26 * |
| $10^{-6}$ | PMA + Ion | 487 ± 37 ** | 557 ± 31 ** | 2663 ± 52 ** |
| $10^{-5}$ | PMA + Ion | 198 ± 35 ** | 144 ± 21 ** | 1465 ± 35 ** |

Note:
Stimulator and BALB/c mouse spleen cells were co-cultured for 24 hours. The cultural supernatant was used to detect the production of cytokine by ELISA method. Data were shown as mean value ± standard error.
* p < 0.05,
** p < 0.01 (two tailed Student's t-test).

The invention claimed is:

1. An artemisinin derivative, wherein the artemisinin derivative is selected from the group consisting of
   3-(12β-artemisininoxy)phenoxy succinic acid;
   ethyl-[4-(12β-artemisininoxy)benzoyl] aminoacetate;
   methyl 2-[4-(12β-artemisininoxy)phenyl] propionate;
   o-methoxy-phenyl 2-[4-(12β-artemisininoxy)phenyl] propionate;
   ethyl 2-[4-(12β-artemisininoxy)phenoxy] propionate;
   2-[4-(12β-artemisininoxy)phenoxy] propanoic acid;
   o-methoxy-phenyl 2-[3-(12β-artemisininoxy)phenoxy] propionate;
   o-methoxy-phenyl 2-[4-(12β-artemisininoxy)phenoxy] propionate; and
   2-[4-(12β-artemisininoxy)phenoxy] propanoic acid.

2. A pharmaceutical composition, which contains a safe and effective dose of the artemisinin derivative of claim 1, and a pharmaceutically acceptable carrier.

3. The pharmaceutical composition of claim 2, wherein the pharmaceutical composition contains 1-55% weight percent of the artemisinin derivative of claim 3, 15-40% weight percent of excipient, and 20-50 weight percent of other conventional auxiliary materials.

4. The pharmaceutical composition of claim 2, wherein the pharmaceutical composition is prepared into the oral, parenteral, pernasal, perlingual, ophthalmic, respiratory tract or rectal dosage forms.

5. The pharmaceutical composition of claim 2, wherein the pharmaceutical composition is prepared into a dosage form selected from the group consisting of tablet, enteric coated pill, sublingual tablet, patch, suppository, cream, ointment, and dermatological gel for skin use.

6. A method of inhibiting T lymphocyte proliferation response and B lymphocyte proliferation response comprising administering to a subject in need of same an effective amount of the artemisinin derivative of claim 1.

\* \* \* \* \*